United States Patent [19]

Levine

[11] Patent Number: 5,344,666
[45] Date of Patent: Sep. 6, 1994

[54] LIQUID DISPENSER

[76] Inventor: Marshall S. Levine, 96 Drummers La., Wayne, Pa. 19087

[21] Appl. No.: 849,903

[22] Filed: Mar. 19, 1992

[51] Int. Cl.⁵ .............................................. B05B 7/24
[52] U.S. Cl. .................................. 427/2.11; 118/300; 118/407
[58] Field of Search ......................... 118/300, 407, 401; 222/80, 82, 185, 181, 613, 420, 457; 604/411, 415, 403, 407; 401/264, 206, 193, 190; 422/102; 427/2, 421

[56] References Cited

U.S. PATENT DOCUMENTS

| | | | |
|---|---|---|---|
| 807,887 | 12/1905 | Walker | 401/193 |
| 887,919 | 5/1908 | Carpenter . | |
| 909,355 | 1/1909 | Wilmore | 222/457 |
| 983,348 | 2/1911 | Carpenter . | |
| 1,152,601 | 9/1915 | Carpenter . | |
| 1,152,602 | 9/1915 | Carpenter . | |
| 2,311,367 | 2/1943 | Chambers . | |
| 2,431,192 | 11/1947 | Munson . | |
| 2,450,225 | 9/1948 | Bernabo . | |
| 2,594,638 | 4/1952 | Goodenow et al. . | |
| 2,608,320 | 8/1952 | Harrison . | |
| 2,667,986 | 2/1954 | Perelson . | |
| 2,679,337 | 5/1954 | Leach . | |
| 2,954,769 | 10/1960 | Callahan et al. . | |
| 3,059,643 | 10/1962 | Barton . | |
| 3,171,446 | 3/1965 | Koch . | |
| 3,203,592 | 8/1965 | Farandatos | 222/80 |
| 3,207,592 | 9/1965 | Harper et al. . | |
| 3,207,774 | 9/1965 | Ziegler et al. . | |
| 3,366,278 | 12/1965 | Fobes | 222/82 |
| 3,482,258 | 12/1969 | Steen . | |
| 3,572,591 | 3/1971 | Brown | 401/190 |
| 3,589,820 | 6/1971 | Ward | 401/193 |
| 3,850,656 | 11/1974 | Brown | 401/190 |
| 3,977,568 | 8/1976 | Smith . | |
| 4,017,007 | 4/1977 | Riccio . | |
| 4,244,467 | 1/1981 | Cavazza . | |
| 4,393,982 | 7/1983 | Kuckens . | |
| 4,413,754 | 11/1983 | Landwehr et al. . | |
| 4473,174 | 9/1984 | Heuser . | |
| 4,552,277 | 11/1985 | Richarson | 604/411 |
| 4,596,572 | 6/1986 | Magrath . | |
| 4,692,151 | 9/1987 | Blackman . | |
| 5,071,034 | 12/1991 | Corbiere . | |
| 5,114,033 | 5/1992 | Golias et al. . | |
| 5,163,583 | 11/1992 | Whitworth . | |

OTHER PUBLICATIONS

Products & Services Section; Thomas Register of American Manufacturers (1992) 2 pgs.

*Primary Examiner*—W. Gary Jones
*Assistant Examiner*—Brenda Lamb
*Attorney, Agent, or Firm*—Weiser & Associates

[57] ABSTRACT

A dispenser for blood and other biological specimens is disclosed which provides a means of obtaining a small predetermined quantity of specimen from a closed container without the need to remove the stopper from the container. The cannula of the device is caused to pierce the container's rubber stopper forming an assembly. When the said assembly is forced against a target surface, such as microscope slide, the force compresses the stopper and thereby reduces the volume inside the container sufficiently to eject a drop of fluid which is dispensed onto a target surface. Stabilizing supports are provided so that fluid emerges from a dispensing tip located a predetermined distance above the target surface which determines the quantity of fluid dispensed. The supports also transmit reactive force from the target surface to compress the rubber stopper of the closed specimen tube.

57 Claims, 2 Drawing Sheets

LIQUID DISPENSER

FIELD OF THE INVENTION

This invention relates generally to the dispensing of liquid biological specimens onto a target surface and more specifically to the dispensing of blood on microscope slides and to the manner in which a small, controlled quantity of fluid is obtained from a closed specimen tube and transferred to a microscope slide for the purpose of making a smear.

DESCRIPTION OF PRIOR DEVICES

In clinical laboratories there is concern about the health hazards of handling blood, i.e., the potential of contracting AIDS and hepatitis and other communicable diseases. When blood smears are prepared, it has been necessary to open the stopper of a specimen tube in order to extract only a single drop. When the tube's rubber stopper is opened, first there is the possibility that hazardous spray or aerosol can occur. Thereafter it is typical to use either glass capillaries or wooden sticks to transfer the blood from the tube to a microscope slide. The procedure creates still more exposed specimen and furthermore it is difficult by either of these methods to easily control the quantity of fluid, thereby creating variation in the uniformity of the resulting blood smears. Lastly, the procedure is slow and inefficient.

To date there are no appropriate alternatives. While a stopper piercing dispenser has been devised, as for example disclosed in U.S. Pat. No. 3,366,278 (Fobes) it is not appropriate for use with blood collection tubes. That is because the device is designed to provide means for syringe-like squeezing action using one hand wherein the thumb or palm engages the bottom of a standard biological container and a finger grip is required by two other fingers of the same hand. However, blood circulation tubes which are of standard configuration the world over are too long to be handled in this manner and the amount of force required is greater than with the biological container.

While it is conceivable to use the cited device in the manner suggested by the proposed invention which forces the dispensing device against the target surface it would be unsuited to having reactive force applied at its dispensing tip. This is because it requires a tip of special design to prevent the formation of a seal against the target surface which would either prevent fluid from exiting or would damage cells due to the pressure. Furthermore, after dispensing fluid, the tip would maintain fluid continuity so that when pressure is relieved a considerable portion of the dispensed fluid would be sucked back. Also, because the dispensing tip of the cited device lacks means to stabilize itself against a target surface, said dispensing tip could, if off-perpendicular forces are applied, easily bend or wander from the location where the liquid is intended to be dispensed.

Furthermore, while the cited patent provides improved control of the quantity of liquid dispensed it does not provide means of dispensing a predetermined quantity and, therefore, in the case of blood usage, smears would be of non-uniform size.

Other devices such as a syringe if employed for this purpose would be both expensive and also hazardous to use because the sharp needle of the typical syringe after removal from the stopper would be full of blood and it would infect a technician if an accident occurred. Furthermore, the syringe is not suited for dispensing exact quantities of fluid, in the 5 micro liter range. Other devices, such as a micro pipets are not designed for piercing stoppers nor do they have the suction capability to extract fluid from a closed specimen tube.

This invention provides a dispenser that is easily adaptable to and connected to existing blood collection tubes, recognizing that existing construction of containers for blood collection normally involves a glass container with a closure or stopper therefor formed of rubber, or other pierceable and resilient material. In this invention the squeezing action is accomplished by manually forcing the container tube and dispenser assembly directly against the target surface.

Thus, it is an objective of the invention to provide a safe and convenient means of dispensing an exact, small quantity of blood from a closed tube without having to remove the stopper or to use wooden sticks or glass capillary tubes.

It is another objective of the invention to provide a liquid dispenser which is readily applied to standard sized, rubber stoppered, closed specimen tube.

It is another objective of this invention to overcome disadvantages of previous inventions to achieve improved mechanical advantage by having the target surface provide the resistive force which in conjunction with applied manual force achieves compression, and for operational efficiency, requiring only the use of a single hand.

It is another objective of this invention to provide exact quantitative control of very small amounts of biological specimens and more generally other liquids as well.

It is another objective of this invention to provide exact quantitative mechanism which can be easily positioned at a desired location on a target surface.

It is another objective of this invention to adequately separate stabilizing supports from the dispensing tip by sufficient distance so that the dispensed fluid does not come in contact with the stabilizing supports, thereby avoiding contamination.

It is another objective of this invention to provide stabilizing supports which are adequately spaced apart to also stabilize against the target surface if force is applied at a non-perpendicular angle.

It is another objective of this invention to provide means for easy viewing of the specimen as it is dispensed.

Another objective of this invention is to provide a cannula which under all conditions of use and misuse is safe, such as by fashioning the cannula with a blunt end and by housing the cannula in a chamber which is large enough to contain said cannula in case it collapses axially in its holder either if subjected to excessive force or due to weak bonding during manufacture, thus preventing the distal end of the cannula from puncturing the user's hand.

Another objective of this invention is to provide convenient surfaces to grasp the device when inserting and removing from the rubber stopper.

These and other objectives will become apparent when the same becomes better understood by reference to the following detailed description when considered in connection with the accompanying drawing wherein:

DESCRIPTION OF THE DRAWING

A preferred embodiment of the invention is shown in the accompanying drawing, in which.

DETAILED DESCRIPTION OF THE PREFERRED EMBODIMENT

Figure 1:
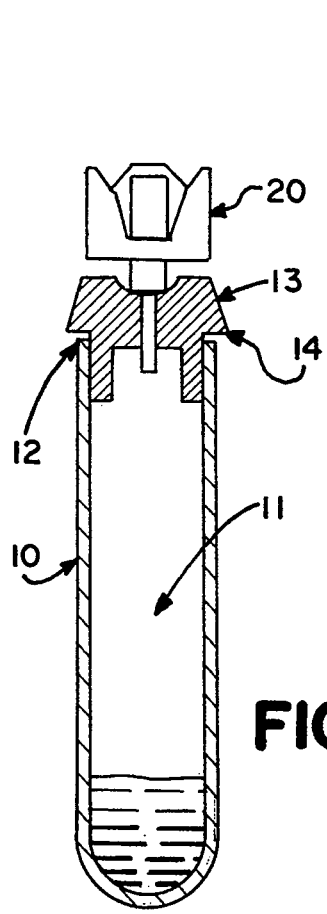
FIG. 1 is a sectional elevational view, in upright position of a typical rubber stoppered container for blood specimen to which is attached an improved dispenser embodying this invention.

Referring now to the drawings there is shown in FIG. 1 containered means includes a stoppered, or normally airtight, container 10 of glass or the like, having an amount of liquid biological specimen 11 therein. The container 10 is provided with an open end 12. A pierceable stopper 13, of rubber or the like is positioned in the open end 12, and the stopper provides a radically enlarged portion 14 which abuts the lip at open end 12. This construction is typical for closed specimen tubes which are manufactured with pre-assembled compressed stoppers. Further, it is known that the tubes are manufactured under reduced atmospheric pressure and that they lose all or most of their vacuum when filled.

FIG. 1 also shows the improved dispenser of this invention mounted on the container means. The improved dispenser is designated generally at 20. The dispenser 20 is constructed to dispense from a relatively large supply thereof shown at 11 in the containered means 10.

Figure 2:
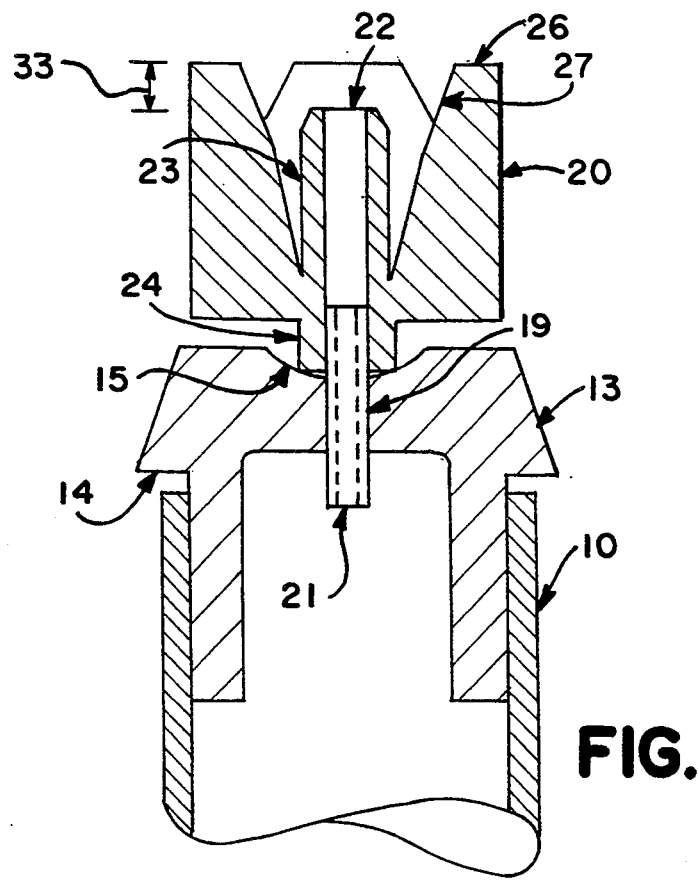
FIG. 2 is an enlarged sectional elevational view illustrating details of construction of the invention in upright position similar to FIG. 1.

Referring now to FIG. 2, details of the invention can be seen. Dispenser 20 includes cannula 19 with an entry tip 21 which is also used for piercing and an exit tube 23 with a dispensing tip 22. There is a pathway from the entry tip 21 to the dispensing tube 22 which communicates fluid. The dispenser 20 is assembled to rubber stopper 13 by pressing entry tip 21 through the center of said stopper when the container is in the upright position. At that time, any pressure difference which might exist between the inside volume and the atmosphere is neutralized.

If cannula 19 is subjected to excessive force said cannula can withdraw or collapse and be safely contained within tube 24. This protects the user from being stuck under accidental conditions.

The dispensing tip 22 is beveled to provide a minimum sized lip surface at the exit, thereby minimizing contamination due to specimen which may remain after use. The entry tip 21 of the cannula 19 has a blunt end to reduce the hazard of accidental sticking of users.

Cannula 19 is held in a boss-like annular abutment member 24 which limits the length of the cannula 19 that can penetrate the rubber stopper. This length is sufficient to penetrate the stopper and enters an additional distance into the well space which is immediately adjacent to the inner surface of the stopper. This additional distance ensures that residue which might collect at the inner surface of the stopper is not sucked into the cannula. The diameter of the annular abutment member 24 is smaller than the average concave diameter of stopper concave depression 15 and the member 24 is also longer than the maximum depth of concave depression 15 of the rubber stopper so that abutment member 24 is always operative to effect a flexing or distortion of rubber stopper 13 to force same inwardly of the container 10.

Flange-like stabilizing supports 26 extend radially outward and axially beyond the end of dispensing tip 22 by a predetermined distance which is related to the amount of dispensed fluid desired. It is obvious that said stabilizing supports 26 may either be integral to the device or that they may be a separable attachment. Also the stabilizing supports 26 may be furnished with an adjustable component so that various gap distances 33 may be selected to determine the quantity of fluid dispensed.

The dispenser 20, may be made of molded material assembled to cannula 19 which may be made of stainless steel or the like. Alternately, the entire device can be made of molded material. Of the said embodiments, the latter typically having a larger cannula diameter is applicable to containers which have in prior use been pre-pierced by a large diameter cannula, such as typically occurs when automatic cell counters equipped with piercing cannula are employed.

Figure 4:
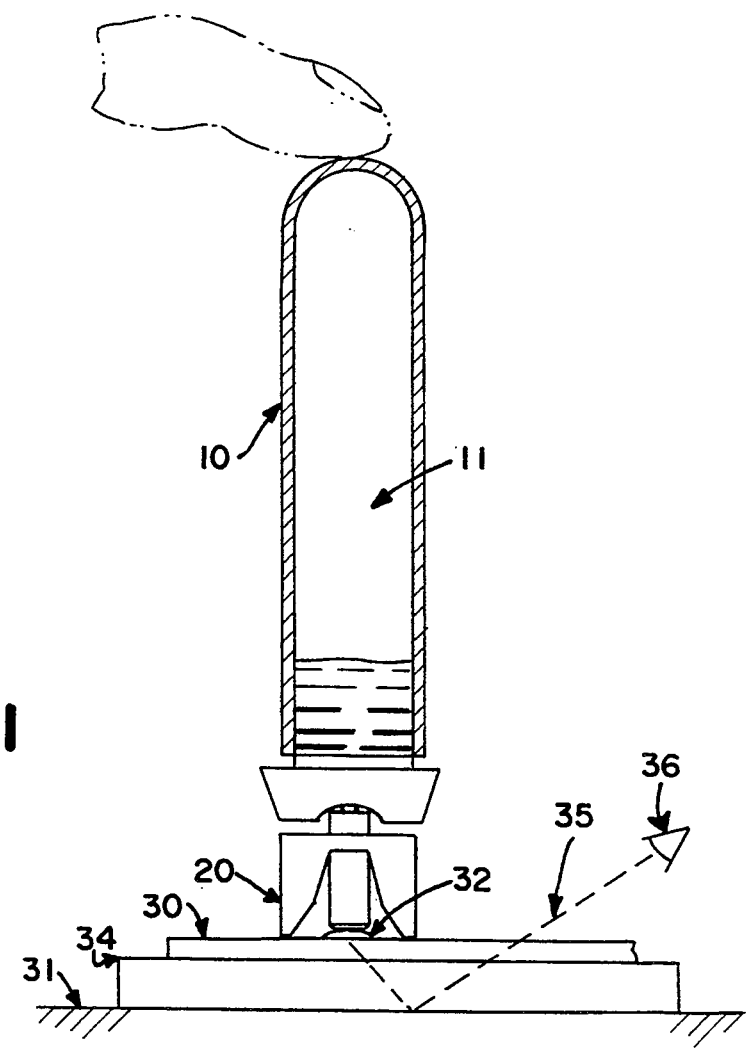
FIG. 4 is a side elevational view showing the dispenser device in inverted position.

Dispenser 20 is very simply connected to the said container means, consisting of container 10 and rubber stopper 20, by forcing the piercing tip 21 through the central portion of rubber stopper 20 until annular abutment member 24 reaches the depth of the concave depression 15 wherein the device is ready for use as seen in FIG. 4.

The use of the device will be understood from the foregoing description and with particular reference being made to FIG. 4. In FIG. 4 the closed tube container with attached device 20 is shown in the inverted operating position, having been assembled in the manner already described. In the inverted position the closed container and the dispenser permit no air to enter so that any attempt by the liquid 11 to escape by force of gravity would have to overcome a partial vacuum which could obviously develop inside closed container 10.

When container 10 with dispenser 20 is pressed by manual force against a target surface, such as glass microscope slide 30 with said target surface supported by optional intermediate member 34 (back surfaced mirror) which in turn is supported by fixed surface 31, such as a counter top, the downward force is resisted by the target surface 30. This creates an internal compression force within the rubber stopper which deforms said stopper, thereby reducing the volume inside container 10 and ejecting a small amount of liquid 32.

In the case of a transparent target surface 30, such as a microscope slide, a back surfaced mirror 34 can be positioned underneath said microscope slide and viewed from above at a convenient angle. The thickness of the mirror glass can be suited to the required viewing angle, wherein thicker glass transposes the image of dispensed fluid 32 a greater distance away from underneath the target location. In FIG. 4 a typical optical path is depicted from the eye 36 of the viewer through the back surfaced mirror 34 through microscope slide 30 to the dispensed fluid 32.

As already described above, the mirror 34 being an intermediate member located between the target surface 30 the counter top 31 permits reactive force from the counter top to be transmitted through the mirror and into the target surface.

Figure 5:
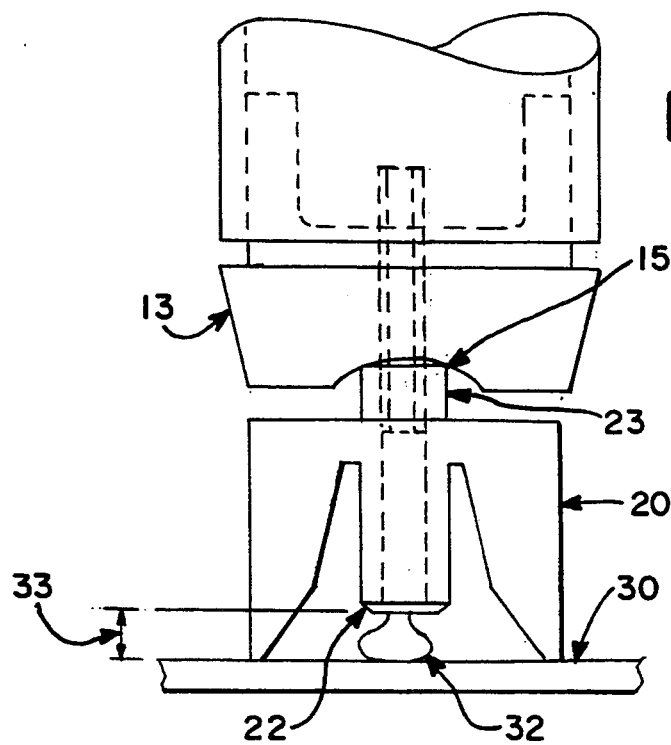
FIG. 5 is an enlarged vertical view of the invention in inverted position showing a drop of fluid forming at the end of its dispenser tip.

Referring now to FIG. 5 it is shown how said compression force is communicated to the rubber stopper 13 by annular abutment member 23 which compresses stopper 13 at the concave depression 15 and distorts the stopper inwardly of the container 10. As described above, the distortion reduces the volume inside container 10 by a very small amount but sufficiently to expel a small volume of fluid to pass through the cannula 19 and out the dispensing tip 22.

FIG. 5 also shows how specimen fluid initially accumulates into drop 32 at the end of dispensing tip 22. When the length of the drop fills gap 33, the bottom surface of said drop touches target surface 30 transferring liquid from dispensing tip 22 to the target surface 30 by the well known action of surface tension. As described earlier, the gap 33 can be made adjustable for applications which require quantities of fluid.

The user can observe when said transfer occurs by viewing through the openings between the support segments 26, which are specifically cut away at all corresponding locations 27. As described earlier, a back surface mirror may also be used for viewing when the target surface is transparent. When the user observes that drop 32 has transferred to the target surface, he or she discontinues force, thereby stopping further flow of fluid. This action can be readily understood as the reverse of the procedure earlier described.

As the fluid drop 32 is transferred to the target surface the fluid path between the dispensing tip 22 and said the target surface 30 will be interrupted. Therefore, the dispensed fluid cannot be sucked back through the dispensing tip 22 such as when force is relieved and the compression of the stopper relaxes. Otherwise such suction would withdraw dispensed fluid back through dispensing tip 22 and through cannula 19 and back into the fluid reservoir 11. Also, as described earlier, air passages surrounding the gap 33 further serve to prevent reversal of flow due to suction.

Figure 3:
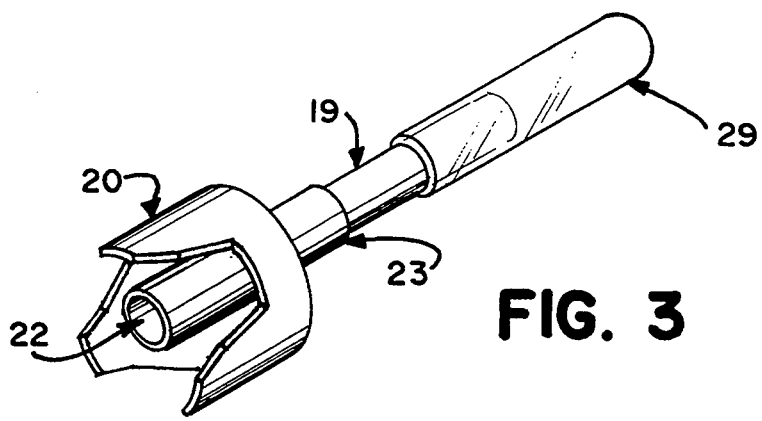
FIG. 3 is a perspective view of the dispenser device showing the protective sheath.

Referring now to FIG. 3 packaging is shown wherein the dispenser 20 can be supplied with a sheath-like tubular element 29 to protect the cannula 19 and to further protect the user as well.

While there has been shown and described a particular embodiment of this invention, it will be obvious to those skilled in the art that various changes and modifications may be made therein without departing from the invention and therefore, it is intended in the appended claims to cover all such changes and modifications as fall within the true spirit and scope of the invention.

I claim:

1. A device for dispensing an amount of fluid from a stoppered container to a target surface, comprising:
a dispenser body having a passageway formed therein, one end of said dispenser body including a surface for engaging said stoppered container and another end of said dispenser body including stabilizing supports for engaging said target surface, and said passageway including means for passing through said stoppered container to interior portions of said stoppered container, for accessing the fluid in said stoppered container and for dispensing said fluid from said passageway and to said target surface responsive to forces applied relative to said dispenser body.

2. The device of claim 1 wherein said means for passing through said stoppered container, for accessing said fluid and for dispensing said fluid from said passageway is a cannula associated with said passageway.

3. The device of claim 2 wherein said cannula includes an entry tip for piercing said stoppered container and for accessing the fluid in said stoppered container.

4. The device of claim 3 wherein said entry tip has a blunt end.

5. The device of claim 3 wherein said dispenser body further includes an abutment member extending from the surface for engaging said stoppered container, for engaging portion of said stoppered container for receiving said abutment member.

6. The device of claim 5 wherein said abutment member is receivable within a concave depression formed in said stoppered container.

7. The device of claim 3 wherein said passageway is sized to fully receive said cannula therein.

8. The device of claim 7 wherein said passageway has a length, said cannula has a length, and wherein the length of said cannula is less than the length of said passageway so that the cannula can collapse into and fully within said passageway.

9. The device of claim 2 wherein said passageway includes an exit tube in communication with said cannula.

10. The device of claim 9 wherein said exit tube includes a dispensing tip for dispensing fluid to said target surface.

11. The device of claim 10 wherein said dispensing tip has a beveled end.

12. The device of claim 10 wherein said stabilizing supports define a plane spaced from said dispensing tip by a defined gap.

13. The device of claim 12 wherein said device includes means for dispensing a predetermined amount of said fluid from said stoppered container.

14. The device of claim 13 wherein said defined gap is proportional to said predetermined amount of fluid to be dispensed from said dispensing device.

15. The device of claim 14 wherein said predetermined amount of fluid is dispensed as a drop having a length which corresponds to said defined gap, for transferring said predetermined amount of fluid directly from said dispensing tip to said target surface responsive to surface tension developed at said target surface.

16. The device of claim 14 wherein said defined gap is adjustable, for regulating said predetermined amount of fluid to be dispensed from said dispensing device.

17. The device of claim 16 wherein said stabilizing supports are adjustable for varying said gap and for varying said predetermined amount of fluid to be dispensed from said dispensing device.

18. The device of claim 11 wherein said stabilizing supports are spaced from each other to define openings to said dispensing tip, for viewing said dispensing tip and for passing air to said dispensing tip.

19. The device of claim 11 wherein said stabilizing supports are positioned at a sufficient distance from said dispensing tip to prevent fluid from contacting said stabilizing supports.

20. The device of claim 2 wherein said cannula is made of plastic.

21. The device of claim 2 wherein said cannula is made of metal.

22. The device of claim 2 wherein said fluid is blood.

23. The device of claim 2 wherein said target surface is a glass slide.

24. A device for dispensing an amount of fluid from a stoppered container, in combination with at stoppered container and a target surface in operative association with said dispensing device, wherein said dispensing device includes a dispenser body having a passageway formed therein, one end of said dispenser body including a surface in contact with said stoppered container and another end of said dispenser body including stabilizing supports in contact with said target surface, and wherein said passageway includes means for passing through said stoppered container to interior portions of said stoppered container, for accessing the fluid in said stoppered container and for dispensing said fluid from said passageway, to said target surface, responsive to forces applied to said stoppered container and developed between said dispensing device and said target surface.

25. The device of claim 24 wherein said means for passing through said stoppered container, for accessing said fluid and for dispensing said fluid from said passageway is a cannula mounted in said passageway.

26. The device of claim 25 wherein said cannula includes an entry tip for piercing said stoppered container and for accessing the fluid in said stoppered container.

27. The device of claim 26 wherein said entry tip has a blunt end.

28. The device of claim 26 wherein said dispenser body further includes means for controlling the amount of penetration of said entry tip.

29. The device of claim 28 wherein said means for controlling the amount of penetration of said entry tip includes an abutment member extending from said surface for engaging said stoppered container, for engaging portions of said stoppered container for receiving said abutment member.

30. The device of claim 29 wherein said abutment member is received within a concave depression formed in said stoppered container.

31. The device of claim 25 wherein said passageway includes an exit tube in communication with said cannula.

32. The device of claim 31 wherein said exit tube includes a dispensing tip for dispensing fluid to said target surface.

33. The device of claim 32 wherein said dispensing tip has a beveled end.

34. The device of claim 32 wherein said stabilizing supports define a place spaced from said dispensing tip by a defined gap.

35. The device of claim 34 wherein said device includes means for dispensing a predetermined amount of said fluid from said stoppered container.

36. The device of claim 35 wherein said defined gap is proportional to said predetermined amount of fluid to be dispensed form said dispensing device.

37. The device of claim 36 wherein said predetermined amount of fluid is dispensed as a drop having a length which corresponds to said defined gap, for transferring said predetermined amount of fluid directly from said dispensing tip to said target surface responsive to surface tension developed at said target surface.

38. The device of claim 32 wherein said stabilizing supports are positioned at a sufficient distance from said dispensing tip to prevent fluid from contacting said stabilizing supports.

39. The device of claim 24 wherein said fluid is blood.

40. The device of claim 24 wherein said target surface is a glass slide.

41. A method for dispensing an amount of fluid from a stoppered container to a target surface utilizing a dispensing device including a body having a passageway for communicating fluid through said dispensing device, a surface for engaging said stoppered container and stabilizing supports for engaging said target surface, an entry tip in communication with said passageway and extending from the surface for engaging said stoppered container, and a dispensing tip formed in said passageway, said method comprising the steps of:
  introducing said entry tip into said stoppered container and bringing said engaging surface into contact with said stoppered container;
  placing said stoppered container and said dispensing device on said target surface so that said dispensing device is in contact with and is positioned over said target surface;
  applying a force against said stoppered container, relative to said target surface, compressing said stoppered container relative to said dispensing device; and
  releasing said force applied against said stoppered container, dispensing said amount of fluid from said dispensing tip and to said target surface.

42. The method of claim 41 wherein said dispensing device includes an abutment member extending from said surface for engaging said stoppered container and said stoppered container includes a concave depression for receiving said abutment surface, and which further comprises the step of introducing said abutment member into said concave depression as said entry tip is introduced into said stoppered container.

43. The method of claim 42 wherein said dispensing device includes a cavity formed in said passageway and sized to fully receive a cannula incorporating said entry tip, and which further includes the step of collapsing said cannula within said cavity responsive to excessive forces applied to said cannula at said entry tip.

44. The method of claim 41 which further includes the step of controlling said amount of fluid dispensed from said dispensing tip to said target surface.

45. The method of claim 44 wherein said controlling is performed by varying a gap defined between the dispensing tip of said dispensing device and said target surface.

46. The method of claim 45 wherein said varying is performed by adjusting said stabilizing supports to vary the height of said dispensing tip relative to said target surface.

47. The method of claim 44 wherein said controlling includes regulating the amount of fluid discharged from said dispensing tip by limiting the size of a drop formed at said dispensing tip in accordance with the gap defined between said dispensing tip and said target surface.

48. The method of claim 47 which further includes the step of transferring said drop directly from said dispensing tip to said target surface.

49. The method of claim 48 wherein said controlling is performed by positioning said stabilizing supports at a sufficient distance from said dispensing tip to prevent dispensed fluid from contacting said stabilizing supports.

50. The method of claim 44 wherein said controlling is performed by positioning said stabilizing supports at a sufficient distance from said dispensing tip to prevent dispensed fluid from contacting said stabilizing supports.

51. The method of claim 50 wherein said controlling is performed by spacing said stabilizing supports from each other to define openings to said dispensing tip.

52. The method of claim 51 wherein said controlling includes passing air through said openings and to said dispensing tip.

53. The method of claim 51 wherein said controlling includes viewing said dispensing tip through said openings and limiting the force applied to said stoppered container to regulate said amount of fluid which is discharged from said dispensing tip.

54. The method of claim 53 wherein said controlling further includes viewing said dispensing tip in a mirrored surface positioned beneath said target surface.

55. The method of claim 54 which further includes the step of varying an apparent distance of said dispensing tip from said target surface by varying the thickness of said mirrored surface.

56. The method of claim 41 wherein said fluid is blood.

57. The method of claim 41 wherein said target surface is a glass slide.

* * * * *

UNITED STATES PATENT AND TRADEMARK OFFICE
CERTIFICATE OF CORRECTION

PATENT NO. : 5,344,666
DATED : September 6, 1994
INVENTOR(S) : Marshall S. Levine and Daniel S. Levine It is certified that error appears in the above-indentified patent and that said Letters Patent is hereby corrected as shown below:

On the cover page, correct item [76] to read:

--[76] Inventors: Marshall S. Levine, 538 Old Eagle School Road, Wayne, Pa. 19087; and Daniel S. Levine, 538 Old Eagle School Road, Wayne, Pa. 19087--.

On the cover page, correct item [22] to read:

--[22] Filed: Mar. 12, 1992--.

Signed and Sealed this

Thirteenth Day of June, 1995

Attest:

BRUCE LEHMAN

Attesting Officer      Commissioner of Patents and Trademarks